United States Patent [19]
Ritter et al.

[11] Patent Number: 5,441,625
[45] Date of Patent: Aug. 15, 1995

[54] ELECTRODE ARRANGEMENT

[75] Inventors: Christoph Ritter; Helmut Zach, both of Graz; Wolf-Dietrich Steinböck, Graz; Susanne Lang, Lannach; Wolfgang Huber, Lieboch, all of Austria

[73] Assignee: AVL Medical Instruments AG, Schaffhausen, Switzerland

[21] Appl. No.: 186,587

[22] Filed: Jan. 26, 1994

[30] Foreign Application Priority Data

Jan. 27, 1993 [AT] Austria ................... 139/93

[51] Int. Cl.⁶ .................................... G01N 27/26
[52] U.S. Cl. .................... 204/409; 204/416; 204/418; 204/435; 204/275
[58] Field of Search ............ 204/409, 416, 417, 418, 204/435, 275

[56] References Cited

U.S. PATENT DOCUMENTS 4,533,456  8/1985  Kratochvil et al. ............... 204/409
4,714,527  12/1987  Hofmeier et al. ................. 204/416

FOREIGN PATENT DOCUMENTS 380741  6/1986  Austria .

*Primary Examiner*—John Niebling
*Assistant Examiner*—Bruce F. Bell
*Attorney, Agent, or Firm*—Watson, Cole, Grindle & Watson

[57] ABSTRACT

An electrode arrangement includes at least one potentiometric measuring electrode located in a sample channel, a reference electrode located in a branch line, and a suction pump downstream of the diaphragmless entrance opening of the branch line into the sample channel the reference electrode being an ion-sensitive, i.e., preferably chloride-sensitive, membrane electrode.

5 Claims, 1 Drawing Sheet

ELECTRODE ARRANGEMENT

BACKGROUND OF THE INVENTION

The invention relates to an electrode arrangement comprising at least one potentiometric measuring electrode located in a sample channel and a reference electrode located in a branch line, a suction pump being provided in the sample channel downstream of the diaphragmless entrance opening of the branch line into the sample channel.

DESCRIPTION OF THE PRIOR ART

Potentiometric measuring electrodes basically necessitate the use of a reference electrode in addition to the potentiometric measuring electrode. The main purpose of this reference electrode is to supply a constant potential, i.e., independent of time and the sample, such that the measuring circuit incorporating the measuring electrode and the reference electrode is influenced only by sample-dependent variations of the potential at the potentiometric measuring electrode. In instances where the potentiometric measuring electrode is not directly immersed in the sample but is separated from it, for example, by a liquid-permeable diaphragm, it is usually possible to provide a relatively simple kind of reference electrode, as this electrode need not be in direct contact with the sample either. In such cases silver/silver-chloride electrodes may be used, for instance. Other examples of simple reference electrodes include applications where the samples may be strongly diluted with a defined solution. As a rule, a supporting electrolyte may be added to the dilute solution, which will always be present in the same concentration. Measuring one of the ions present in the supporting electrolyte by means of a suitably selective potentiometric electrode may then provide the reference electrode potential.

The development of reference electrodes for use in undiluted samples is much more complicated, since it is virtually impossible to fully satisfy the requirement for an ever constant potential at the reference electrode. To a degree this requirement is fulfilled by using a two-part reference electrode: First, an electrode of greatest possible stability is used (e.g., calomel electrodes or, sometimes, electrodes of silver/silver-chloride). This electrode is in contact with a liquid, which in turn will establish the contact with the sample to be measured and is characterized by very high salt concentrations of a salt where anions and cations have largely identical mobilities. As a result of these identical mobilities of anions and cations, the potential at the interface between this liquid and the sample is very small. The high salt concentrations will reduce the significance of concentration variations in the sample. A popular liquid used for such purposes is concentrated potassium chloride solution (KCl). If the reference electrodes are required for long-term usage, the silver/silver-chloride-type electrode is not suitable as a rule, as its long-term stability cannot be guaranteed. For this reason a calomel electrode is preferred in such instances.

Such reference electrodes, consisting of concentrated salt solutions of similar mobilities, and of a calomel electrode, have been used successfully for many years, although there are some practical problems, such as, (a) The interface between the reference electrolyte (KCl) and the sample, which is represented by a diaphragm, is a critical zone which may easily be plugged, clogged, etc., thus giving rise to measuring errors.

(b) The calomel electrode is a relatively sensitive component as regards its production and handling, since the materials (mercury, calomel, cotton wool) must be introduced with great care and protected from shock during transport and operation.

(c) Another aspect is the growing awareness of environmental hazards, which produces a critical attitude towards the use of mercury.

(d) In order to keep the calomel electrode ready for use, it must be stored in a liquid corresponding to the one in which it is to be immersed (concentrated KCl).

SUMMARY OF THE INVENTION

It is an object of the invention to propose an electrode arrangement of simple configuration, which is easy to handle during storage, transport and operation, and which eliminates the danger of clogging or plugging at the interface between reference electrolyte and sample, thus ruling out measurement errors.

In the invention this object is achieved by configuring the reference electrode as an ion-sensitive, preferably chloride-sensitive membrane electrode. Whereas the configuration of a calomel electrode is essentially defined and can hardly be modified, leaving only limited scope for miniaturization, the configuration of an ion-selective membrane electrode is characterized by great simplicity, additional advantages being dry storage, long life and the possibility of miniaturization of the electrode. The sensitive membrane is essentially made of polyvinyl chloride (PVC) and ion-exchange material. For example, the reference electrode of the invention may be coated with a chloride-sensitive membrane as described in AT-PS 380 741.

Ion-sensitive PVC membranes unusally require that a liquid contact be established with the lead wire on the side of the membrane facing away from the sample in order to obtain a potential of maximum stability (transition from the ionic conductor to the electronic conductor). The advantage of a chloride-sensitive membrane is that it permits direct contact with a silver/silver-chloride wire without the use of an intermediate liquid. This will considerably simplify the building of such an electrode. The reason for this is the existence of electrochemically defined conditions for all phase transitions (the chloride membrane is in equilibrium with the silver/silver-chloride layer, the silver/silver-chloride layer is in equilibrium with the silver wire). Since membranes made of PVC-ionic exchanger are hardly subject to drifting at the beginning of measurement, this type of electrode, unlike calomel electrodes, need not be kept in contact with the electrolyte during storage. In further development of the invention a valve is provided in each of the branch line and the sample channel, and the two valves together with the suction pump are connected to a control unit. It is recommended that the valves be placed upstream of the reference electrode and the measuring electrode.

As is mentioned in the context of prior art arrangements, diaphragms are used as a rule in order to minimize KCl consumption. Such diaphragms are easily clogged, however. For this reason it is proposed that the interface between sample and reference electrolyte be configured as a simple T-piece, permitting a small amount of electrolyte (KCl) to be sucked in after the sample has been drawn into the sample channel and come to rest, i.e., by adequately controlling a suction pump and two valves, in order to make sure that fresh reference electrolyte is provided at the interface between the sample and the reference electrolyte for each new measurement. The diameter of this T-connection may be a few tenths of a millimeter.

In this way the electrode arrangement described above is provided with a long-life, maintenance-free reference electrode permitting dry storage, which is ideally suited for measuring biological samples, for instance.

DESCRIPTION OF THE DRAWINGS

Following is a more detailed description of the invention with reference to the accompanying drawings, in which.

DETAILED DESCRIPTION OF THE PREFERRED EMBODIMENT

Figure 1:
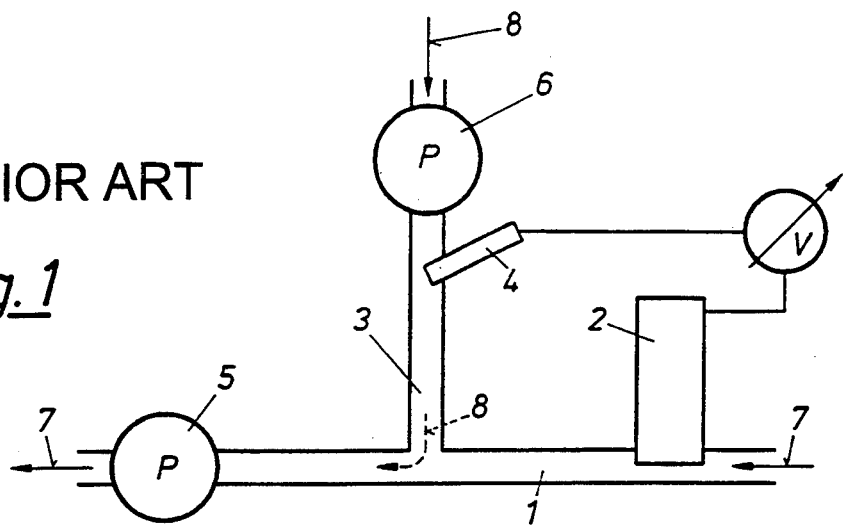
FIGS. 1 and 2 show prior art electrode arrangements.

In the known type of electrode arrangement shown in FIG. 1 a potentiometric measuring electrode 2 is located in a sample channel 1. A branch line 3 branching off from the sample channel 1 in a tee contains a calomel electrode as reference electrode 4, closing the measuring circuit towards the measuring electrode. The sample is delivered by means of a suction pump 5, while a pump 6 is used for providing the calomel electrode with KCl. The direction of sample transport is indicated by arrows 7, that of electrolyte transport by arrow 8.

Figure 2:
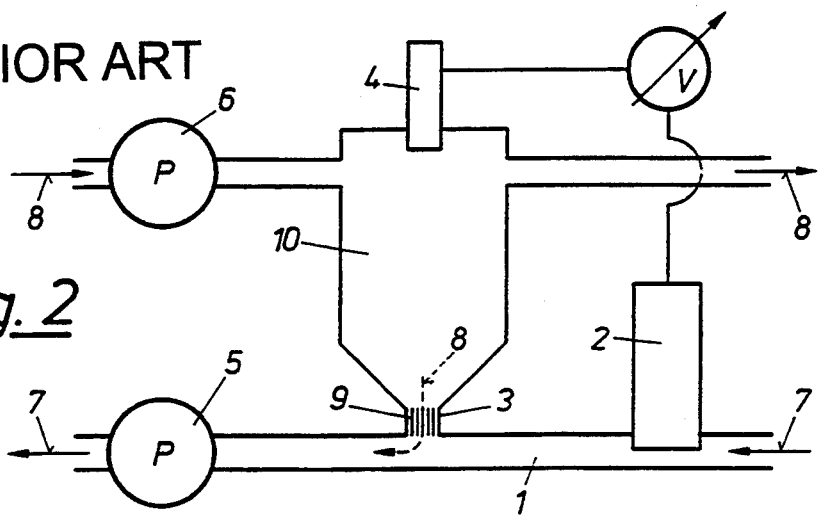

Another known type of electrode arrangement is shown in FIG. 2, where the interface between sample and reference electrolyte is established with the use of a diaphragm 9 or a capillary, to keep down KCl consumption. The sample is prevented from entering the container 10 with the calomel electrode 4 and the electrolyte by a slight excess pressure generated by the pump 6.

Figure 3:
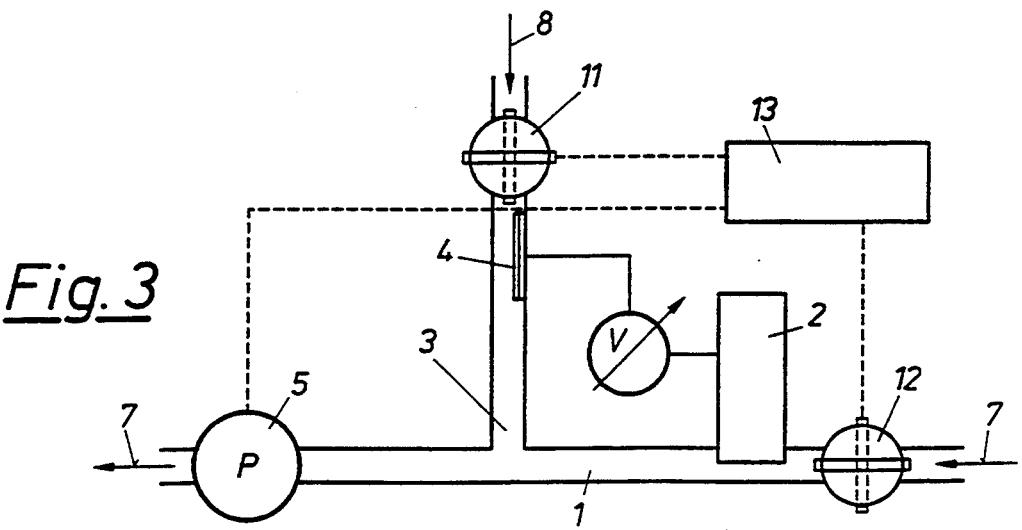
FIG. 3 shows an electrode arrangement of the invention.

The electrode arrangement of the invention, which is shown in FIG. 3 and has reference numbers corresponding to those of the prior art variants, is provided in its branch line 3 with a reference electrode 4 configured as an ion-sensitive membrane electrode, the entry of the branch line 3 into the sample channel 1 being configured as a diaphragmless opening whose diameter is >0.2 mm. For the arrangement of FIG. 3 only one suction pump 5 is required, as the streams of sample and reference medium are controlled by means of a valve 11 and 12, respectively, which are located in the branch line 3 and in the sample channel 1, and are connected to a control unit 13 together with the suction pump 5.

We claim:

1. An electrode arrangement comprising at least one potentiometric measuring electrode located in a sample channel and a reference electrode located in a branch line branching off from said sample channel with a diaphragmless entrance opening having a diameter greater than 0.2 mm, a single suction pump provided in said sample channel downstream of said diaphragmless entrance opening of said branch line into said sample channel to suck at least one of a liquid sample through said sample channel and a reference liquid through said branch line, wherein a valve is provided each in said branch line and said sample channel, and wherein said valves together with said suction pump are connected to a control unit, and wherein said reference electrode is configured as an ion-sensitive membrane electrode.

2. An electrode arrangement according to claim 1, wherein said ion-sensitive membrane electrode is a chloride-sensitive membrane electrode.

3. An electrode arrangement according to claim 2, wherein said chloride-sensitive membrane electrode comprises a chloride-sensitive membrane in direct contact with a silver/silver-chloride wire.

4. An electrode arrangement according to claim 1, wherein said first and second valves are placed upstream of said measuring electrode and said reference electrode, respectively.

5. A potentiometric electrode apparatus for liquid samples which includes only a single suction pump, said apparatus comprising;
   a first conduit means which provides a channel through which a liquid sample can pass in a first downstream direction,
   a potentiometric electrode located in said first conduit means to contact liquid sample in said first conduit means,
   a second conduit means connected to said first conduit means downstream of said potentiometric electrode at an entrance opening having a diameter greater than 0.2 mm and no diaphragm therein, a reference liquid passing through said second conduit means in a second downstream direction into said first conduit means,
   an ion-sensitive reference electrode located in said second conduit means,
   a single suction pump means connected to said first conduit means downstream of said entrance opening to suck at least one of said liquid sample through said first conduit means in said first downstream direction and said reference liquid through said second conduit means in said second downstream direction,
   a first valve means connected in said first conduit means to control flow of liquid sample therethrough,
   a second valve means connected in said second conduit means to control flow of reference liquid therethrough, and
   control means connected to said first and second valve means to control opening and closing thereof and connected to said single suction pump to control operation thereof.

* * * * *